US006436051B1

(12) United States Patent
Morris et al.

(10) Patent No.: US 6,436,051 B1
(45) Date of Patent: Aug. 20, 2002

(54) ELECTRICAL CONNECTION SYSTEM FOR ULTRASONIC RECEIVER ARRAY

(75) Inventors: Richard Franklin Morris, Stoughton; Steven Taylor Morris, Madison; Duane Anthony Kaufman, Hollandale, all of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/910,325

(22) Filed: Jul. 20, 2001

(51) Int. Cl.[7] .................................................. A61B 8/00
(52) U.S. Cl. ....................... 600/459; 29/25.35; 600/437
(58) Field of Search ................................. 600/459, 437, 600/449; 29/25.35

(56) References Cited

U.S. PATENT DOCUMENTS

| | | | | |
|---|---|---|---|---|
| 4,930,511 A | | 6/1990 | Rossman et al. | |
| 5,617,866 A | * | 4/1997 | Marian, Jr. | 439/66 |
| 5,840,029 A | * | 11/1998 | Mazess et al. | 600/437 |

* cited by examiner

*Primary Examiner*—Francis J. Jaworski
*Assistant Examiner*—Ruby Jain
(74) *Attorney, Agent, or Firm*—Quarles & Brady LLP

(57) ABSTRACT

A connector assembly for a thin film acoustic receiver array provides a spring support block having a plurality of holes each aligning one helical compression spring which serves as a conduit between a rear surface of the piezoelectrict film and a circuit card. The front surface of the film is supported against the force of the springs using an acoustically transparent material that may also provide matching between water and the piezoelectric film

20 Claims, 3 Drawing Sheets

ELECTRICAL CONNECTION SYSTEM FOR ULTRASONIC RECEIVER ARRAY

CROSS-REFERENCE TO RELATED APPLICATIONS

N/A

STATEMENT REGARDING FEDERALLY SPONSORED RESEARCH OR DEVELOPMENT

N/A

BACKGROUND OF THE INVENTION

The present invention relates to ultrasonic receiver arrays for use in imaging ultrasonic devices and, in particular, to an improved method of providing electrical connection for such receiver arrays.

Ultrasound may be used to characterize living tissue through the attenuation, change in speed of sound, or other modification of ultrasonic energy through the tissue. A device using this approach for quantitative measurement of bone quality, such as may be useful in the study and treatment of osteoporosis, provides an ultrasonic transmitter positioned across from an ultrasonic receiver about a volume which may receive a portion of the body containing bone with high trabecular content. A convenient site for such a measurement is the os calcis of the human heel, which includes substantial trabecular bone structure and minimal intervening soft tissue.

It can be desirable to combine the capability of imaging and quantitative measurement to an ultrasonic device, for example, to allow the operator to ensure correct foot location and thus improve repeatability in measurements taken at different times. U.S. Pat. No. 6,027,449, entitled: "Ultrasonometer Employing Distensible Membranes", assigned to the assignee of the present case and hereby incorporated by reference, describes a method of manufacturing an ultrasound detection array using a thin film of piezoelectric material plated with regularly spaced electrodes. The electrodes are attached to processing circuitry using acoustically transparent Mylar connectors. Such connectors provide extremely high quality connection with minimal acoustic disruption, but can be difficult to manufacture. What is needed is an alternative connection method that provides high reliability, linearity, and stability.

BRIEF SUMMARY OF THE INVENTION

The present invention provides a contact system for film-type piezoelectric material permitting simplified manufacturing. The piezoelectric film is supported on its front face by an acoustically transparent material and a set of springs are sandwiched between the rear face of the piezoelectric film and a circuit board having processing circuitry, to provide electrical connection therebetween. The springs may be pre-assembled in a carrier by vibratory or other automatic assembly techniques and provide for high areal density interconnection with moderate effect on the acoustic signal.

Specifically, the present invention provides an ultrasonic array using a piezoelectric sheet having a plurality of electrodes spaced at predetermined array locations on a rear surface of the sheet. A set of electrically independent conductive springs are positioned at the array locations and a circuit card having electrical terminals positioned at the array location on a front side of the circuit card, is placed proximate thereto. A retention frame compresses the array of conductive springs between the piezoelectric sheet and the circuit card to establish electrical communication between the electrodes and terminals.

In this way, an acoustically light and readily manufactured connection is made.

An acoustically transparent support block may be fastened to a front surface of the piezoelectric material. This block allows the thin film piezoelectric material to resist the pressure of the springs. The block may further provide for impedance matching from water coupling material to the piezoelectric film. In this regard, the support block may have an acoustic impedance between the acoustic impedance of the piezoelectric sheet and the acoustic impedance of water.

The circuit card may include at least one multiplexer circuit on the second side of the circuit card opposite the terminals but communicating with the terminals and for selectively collecting at least one communication lead to ones of the terminals.

In this way, the high density of connections may be converted to a convenient number of leads and the circuitry for doing so may be displaced from acoustic contact with the piezoelectric film.

The device may include a spring support plate positioned between the film and the circuit card having a series of axial holes sized to support the springs in position at the array locations. A means for maintaining an air gap positioned between the spring support plate and the film may be provided.

In this way, the springs may be supported to improve manufacturability of the device without interfering with the acoustic properties of the connection.

The array locations may be interstices of a rectangular grid separated by less than one-half centimeter.

Thus, the present invention can provide extremely high connection densities.

The foregoing features and advantages may not apply to all embodiments of the inventions and are not intended to define the scope of the invention for which purpose claims are provided. In the following description, reference is made to the accompanying drawings, which form a part hereof, and in which there is shown by way of illustration, a preferred embodiment of the invention. Such embodiment also does not define the scope of the invention and reference must be made therefore to the claims for this purpose.

DETAILED DESCRIPTION OF THE PREFERRED EMBODIMENT

Figure 1:
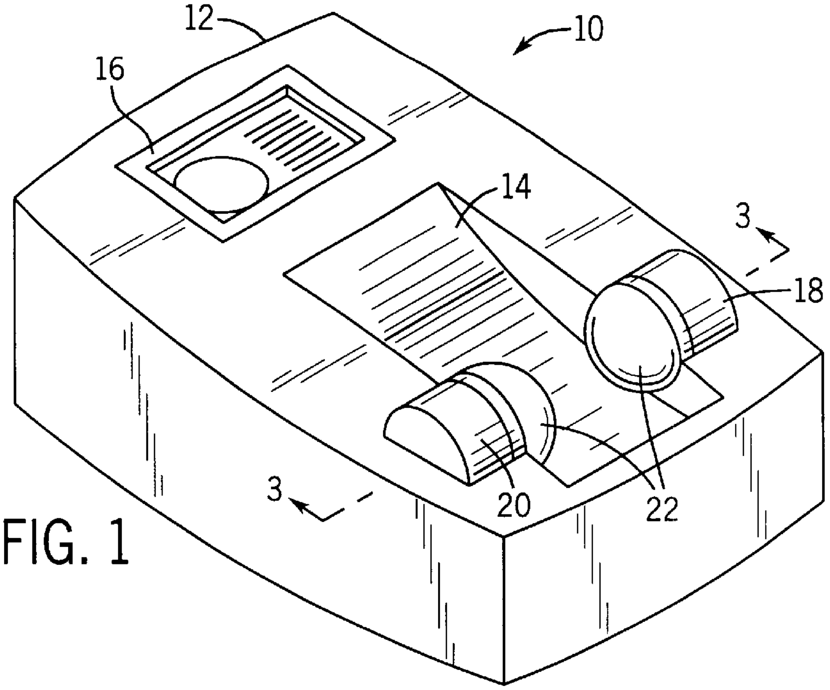
FIG. 1 is a perspective view of an imaging/quantitative ultrasonic densitometer suitable for use with the present invention showing an ultrasonic reception unit and ultrasonic transmission unit opposed across a footwell.

Referring to FIG. 1, an imaging/quantitative ultrasonic device 10 includes a housing 12 having a generally upward opening footwell 14 sized to receive a human foot. At the toe end of the footwell 14 on the upper surface of the housing 12 is a display/touch panel 16 allowing data to be entered into or received from an internal computer (not shown in FIG. 1). Flanking the footwell 14 near the heel end of the footwell is an ultrasonic transmitter unit 18 and an ultrasonic receiver unit 20 supporting at their opposed surfaces compliant bladders 22 holding a coupling fluid such as water. The bladders 22 serve to communicate ultrasonic energy from the contained transducers of the transmitter unit 18 through a patient's foot inserted into the footwell 14 and back out to the contained transducer of the receiver unit 20.

Figure 3:
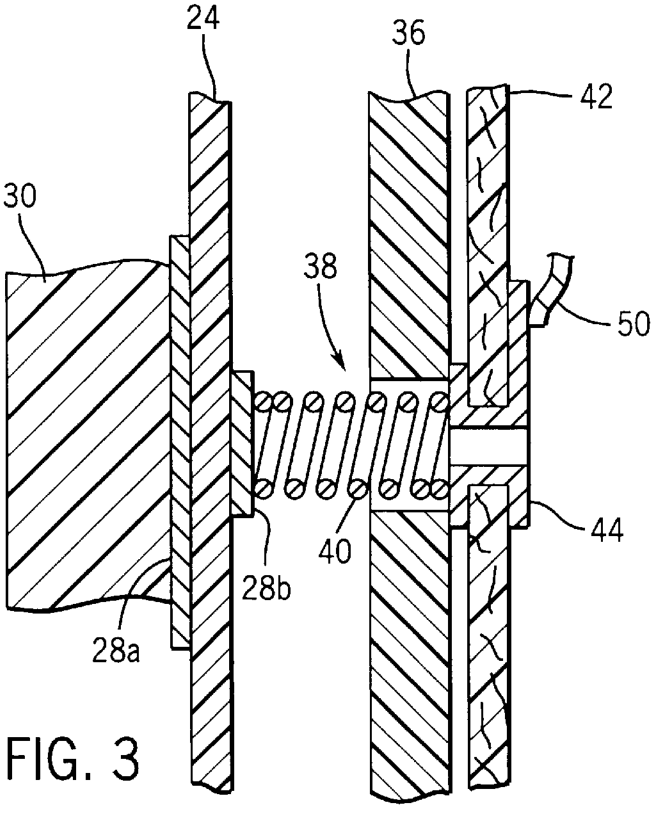
FIG. 3 is a fragmentary cross-section of the reception unit of FIG. 1 along line 3—3 showing the compression of the springs as held by the spring retention plate between the film and the circuit board.
Figure 2:
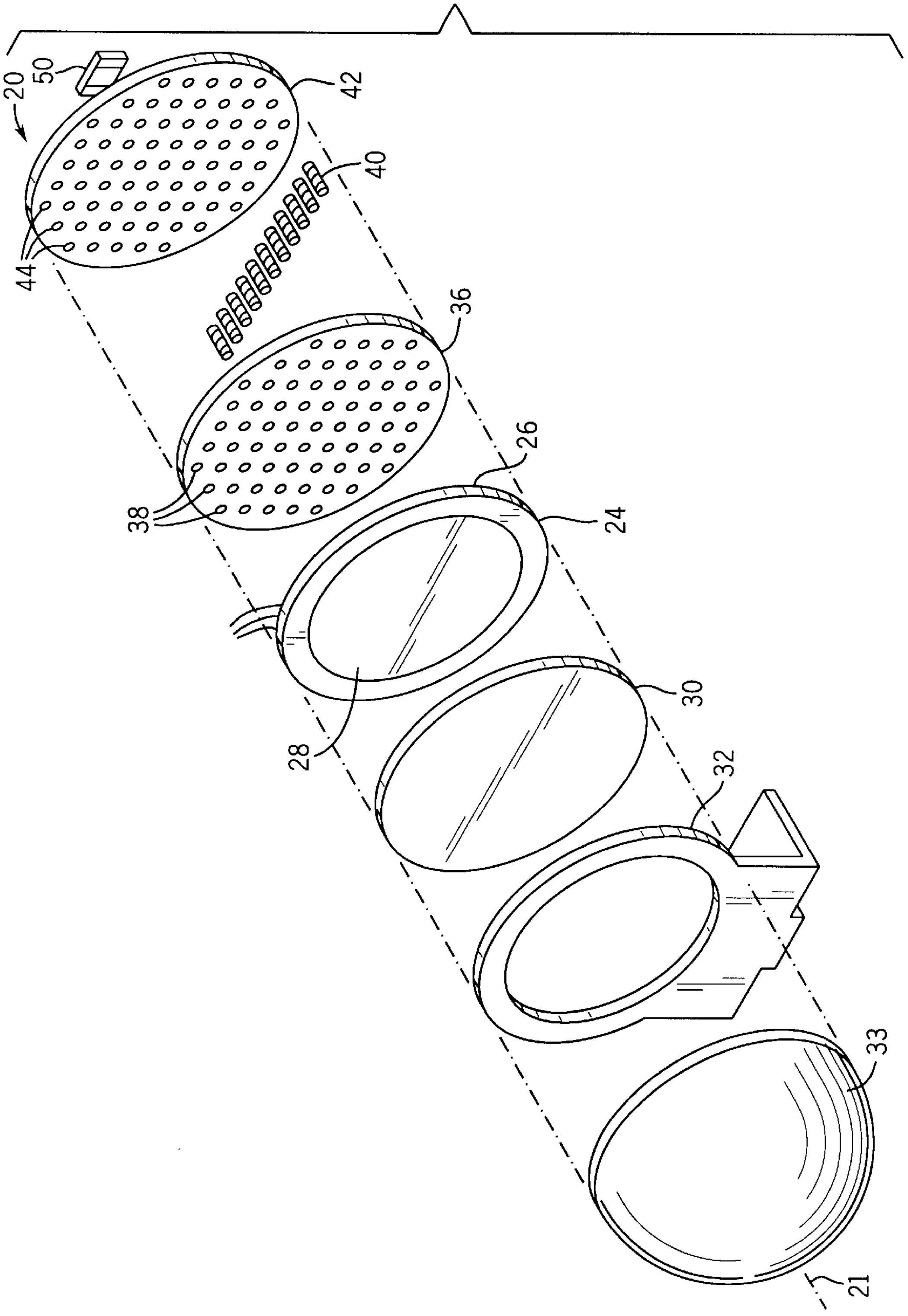
FIG. 2 is an exploded perspective view of the ultrasonic reception unit of FIG. 1 showing the constituent thin film transducer attached to a coupling plate and compliant water filled bladder, on one side, and attached via a spring array and spring retention plate to a circuit card, on the other side.
Figure 4:
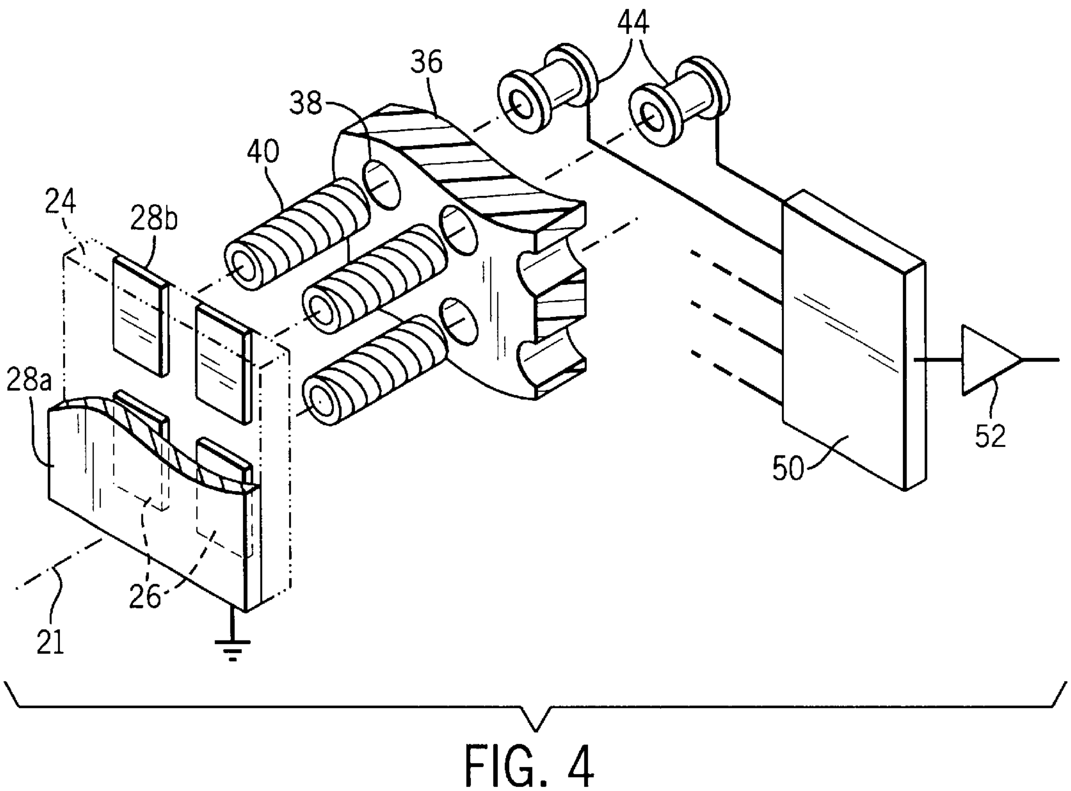
FIG. 4 is a perspective view of the fragment of FIG. 3 showing the electrical connection of the multiplexers through plate-through holes of the circuit card.

Referring now to FIGS. 2, 3 and 4, the receiver unit 20 may include a piezoelectric sheet 24 of circular outline positioned normal to a transmission axis between the receiver unit 20 and transmitter unit 18.

The piezoelectric sheet 24 is divided into a number of transducer elements 26 defined by electrodes 28 placed on opposite surfaces of the piezoelectric sheet 24. Rear electrodes 28b are deposited by vacuum metallization and may be squares centered at the interstices of a rectangular grid to fall in rectilinear rows and columns. A solid continuous electrode 28a is positioned on the opposite side of the piezoelectric sheet 24. The center of each rear electrode 28b is separated from its neighbor by less than one-half centimeter and the front electrode 28a is connected to a common reference voltage.

The piezoelectric sheet 24 may be constructed polyvinylidene fluoride (PVDF). In manufacture, the piezoelectric sheet 24 is polarized to create its piezoelectric properties by heating and cooling the sheet in the presence of a polarizing electric field according to methods well understood in the art. In the preferred embodiment, the entire sheet is thus polarized, however it may be advantageous to 'spot polarize' the sheet where only the areas under the metalization are piezoelectric providing for better cross talk isolation according to polarization methods well known in the art. Mechanical forces operating on the piezoelectric sheet 24 create a voltage between electrodes *28a* and *28b*.

Attached to the front of the piezoelectric sheet 24 in the direction of received ultrasonic energy is a matching plate 30 constructed of an acoustically transmitting material, such as a polyester, having a speed of sound near that of water and the piezoelectric sheet 24 to provide for improved matching between the two. The thickness of the matching plate 30 is arbitrary but chosen to be many times the operating wave length of the ultrasound so as to delay any reverberation effects that may occur due to acoustic impedance mismatches, and to be sufficiently thick so as to withstand reasonable pressure from water on its front side, as will be described, mechanical shock to which the imaging/quantitative ultrasonic device 10 may be subjected, and the combined pressure of connector springs, also to be described. In the preferred embodiment, the matching plate 30 is generally planar, however, lens shaped plates providing a focusing of acoustic energy may also be used.

Referring again to FIG. 2, the piezoelectric sheet 24 and matching plate 30 are attached together with an adhesive and fit within a retainer ring 32 that provides a point of attachment for the receiver unit 20 to the housing 12. The retainer ring 32 also provides a flange on its front surface holding a compliant silicon bladder 33 filled with water to provide a coupling path for ultrasonic energy from the heel of the patient through the matching plate 30 to the piezoelectric sheet 24. Ports in the retainer ring 32 (not shown) allow inflation of the bladder before use and deflation of the bladder for storage.

Referring still to FIGS. 2 and 4, a spring holder 36 is positioned behind the piezoelectric sheet 24 opposite the matching plate 30. The spring holder 36 is comprised of an insulating disk such as a plastic and having a plurality of axial holes 38, each aligned with one electrode *28b*, and each hole sized to hold a helical compression springs 40.

The springs 40 may be loaded into the holes 38 of the spring holder 36 by a vibratory feeder or other assembly technique and held in position for assembly by the introduction of a volatile liquid such as alcohol, which acts to retain the springs 40 by surface tension. Each spring 40 is otherwise free to move axially within the holes 38.

Behind the spring holder 36 is a circuit board 42 which may be an epoxy glass material well known in the art. The front surface of the circuit board 42 has a number of terminal pads being part of plate through holes 44 passing through the circuit board 42. Each of the plate through holes 44 aligns with one of the axial holes 38 and with an electrode *28b* so that the spring 40 may provide a path from electrode *28b* to a plate through hole 44.

The circuit board 42 is held adjacent to the piezoelectric sheet 24 by the retainer ring 32 in a manner such that there is an air space between the front surface of the spring holder 36 and the rear surface of the piezoelectric sheet 24 so as to reduce the conduction of ultrasonic energy out of the piezoelectric sheet 24 into the spring holder 36. Springs 40, while not as light as aluminized Mylar, provide an acceptably reduced conduction of ultrasonic energy away from piezoelectric sheet 24.

The plate through hole 44 provides a conduit, shown in FIG. 3, conducting electrical energy to the rear side of the circuit board 42 where it may be connected to the lead of a multiplexer 50, the latter soldered onto a terminal or trace on the rear of the printed circuit board according to techniques well known in the art. Referring to FIG. 4, the multiplexers 50 allow selective connection of one or more transducer element 26 at a time to an output lead 52. This selective connecting may read, in a scanning process, the voltage at each electrode *28b*.

Figure 5:
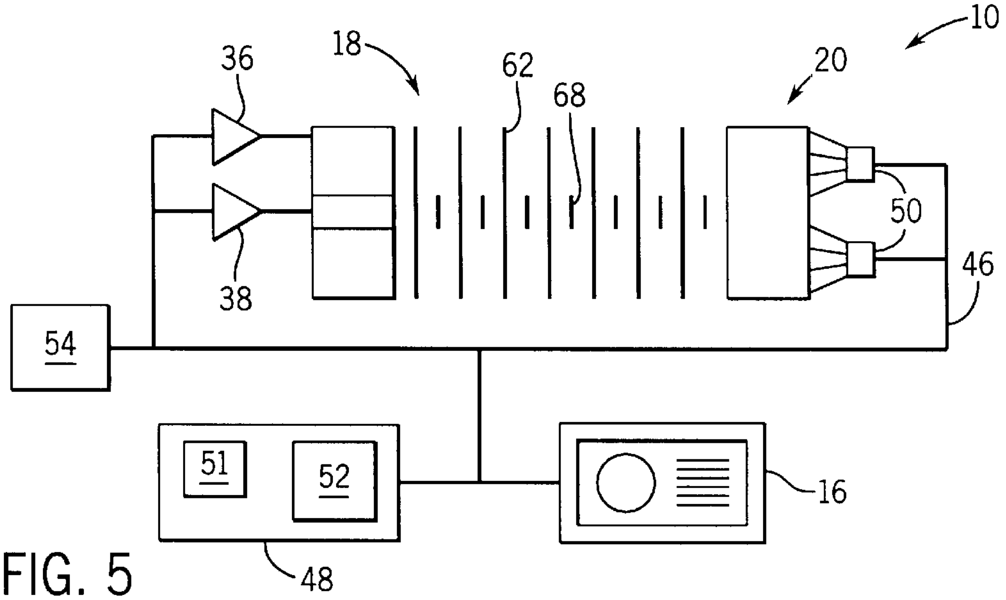
FIG. 5 is a schematic representation of the densitometer of FIG. 1 showing the control of the transmitter unit and the receiver unit by a microprocessor, which also controls mechanical subsystems and a display.

Referring now to FIG. 5, an imaging/quantitative ultrasonic device 10 incorporating the receiver unit 20 provides an internal bus 46 allowing a computer 48 having a processor 50 and memory 53 to communicate both with the transmitter unit 18 and the receiver unit 20. In this way, the transmitted wave may be controlled according to a program held in memory 53 and the received wave may be processed according to the program in memory 53. The bus 46 also communicates with the display/touch panel 16 which allows inputting of data to the computer 48 and outputting data from the computer 48 during execution of the program in memory 53. The bus 46 also allows communication between the computer 48 and the mechanical subsystems 54 such as pumps for inflating the bladders 33 prior to use or deflating the bladders 33 for storage.

During operation of the program held in memory 53, the computer 48 energizes the ultrasonic transmitter unit 18 to produce a generally planar wave 62 for imaging purposes. The computer 48 scans the multiplexers 50 through the transducer elements 26 of the receiver unit 20 to collect and process image data. This image data may consist of attenuation data such as broadband ultrasonic attenuation (BUA) or speed of sound measurements (SOS), a combination of both, or some other acoustic parameter, mapped to a gray scale value and a spatial location in the image corresponding to the location of each transducer element 26 in the ultrasonic receiver unit 20. The image may be displayed on the display/touch panel 16.

It is specifically intended that the present invention not be limited to the embodiments and illustrations contained herein, but that modified forms of those embodiments including portions of the embodiments and combinations of elements of different embodiments also be included as come within the scope of the following claims.

What is claimed is:

1. An ultrasonic array comprising:

a piezoelectric sheet having a plurality of electrodes spaced at predetermined array locations on a rear surface of the sheet;

an array of electrically independent conductive springs positioned at the array locations;

a circuit card having electrical terminals positioned at the array locations on a front side of the circuit card; and a retention means compressing the array of conductive springs between the piezoelectric sheet and the circuit card to establish electrical communication between the electrodes and terminals.

2. The ultrasonic array of claim 1 including an acoustically transmissive support block fastened to a front surface of the piezoelectric sheet.

3. The ultrasonic array of claim 1 wherein the support block has a speed of sound near that of the piezoelectric sheet and water.

4. The ultrasonic array of claim 1 wherein the support block is polyester.

5. The ultrasonic array of claim 1 wherein the piezoelectric sheet is PVDF.

6. The ultrasonic array of claim 1 including at least one multiplexer circuit communicating with the terminals for selectively connecting at least one communication lead to ones of the terminals, the multiplexer positioned on a second side of the circuit card opposite the terminals.

7. The ultrasonic array of claim 1 wherein the springs are helical compression springs.

8. The ultrasonic array of claim 1 wherein the springs are gold plated.

9. The ultrasonic array of claim 1 including a spring support plate positioned between the film and the circuit card and having a series of axial holes sized to support the springs in position at the array locations.

10. The ultrasonic array of claim 9 including means for maintaining an air gap positioned between the spring support plate and the film.

11. The ultrasonic array of claim 1 wherein the array locations are the interstices of a rectangular grid.

12. The ultrasonic array of claim 1 wherein the array locations are less than 5 millimeters apart.

13. The ultrasonic array of claim 1 wherein the ultrasonic array is a receiver array and wherein the multiplexer further communicates with an input circuit for collecting data from the ultrasonic array.

14. The ultrasonic array of claim 1 further including an ultrasonic transmitter positioned to transmit ultrasonic acoustic waves to the ultrasonic array and including a processor executing a stored program to receive data from the ultrasonic array to provide measurements of in vivo bone.

15. A method of manufacturing an ultrasonic array comprising the steps of:

(a) preparing a piezoelectric sheet with a plurality of electrodes spaced at predetermined array locations on a rear surface of the sheet;

(b) positioning an array of electrically independent conductive springs at the array locations; and (c) compressing the array of conductive springs between the piezoelectric sheet and a circuit card having electrical terminals positioned at the array locations on a front side of the circuit card to establish electrical communication between the electrodes and terminals.

16. The method of manufacturing recited in claim 15 including a step before step (c) of attaching an acoustically transmissive support block to a front surface of the piezoelectric sheet.

17. The method of manufacturing recited in claim 15 including the step of attaching at least one multiplexer circuit with the terminals for selectively connecting at least one communication lead to ones of the terminals, the multiplexer positioned on a second side of the circuit card opposite the terminals.

18. The method of manufacturing recited in claim 15 including the step of gold plating the springs.

19. The method of manufacturing recited in claim 14 including the steps of inserting the array of springs in an insulating spring support plate and then positioning the spring support plate between the film and the circuit card and having a series of axial holes sized to support the springs in position at the array locations.

20. The method of manufacturing recited in claim 19 including the step of locating the spring support plate to provide an air gap between the spring support plate and the film.

* * * * *